(12) United States Patent
Bertz et al.

(10) Patent No.: US 7,964,201 B2
(45) Date of Patent: Jun. 21, 2011

(54) PERSONAL CARE COMPOSITIONS

(75) Inventors: Steven H. Bertz, Morristown, NJ (US); Ilya Makarovsky, Fair Lawn, NJ (US)

(73) Assignee: ISP Investments Inc., Wilmington, DE (US)

( * ) Notice: Subject to any disclaimer, the term of this patent is extended or adjusted under 35 U.S.C. 154(b) by 1168 days.

(21) Appl. No.: 11/128,020

(22) Filed: May 12, 2005

(65) Prior Publication Data

US 2006/0024254 A1 Feb. 2, 2006

Related U.S. Application Data

(60) Provisional application No. 60/598,211, filed on Aug. 2, 2004.

(51) Int. Cl.
*A61K 8/03* (2006.01)
*A61K 8/06* (2006.01)
*A61K 8/20* (2006.01)

(52) U.S. Cl. ......... 424/401; 424/70.1; 424/59; 514/884; 514/847; 514/937; 514/943

(58) Field of Classification Search ............... 424/401, 424/70.1, 59; 514/844, 847, 937, 943
See application file for complete search history.

(56) References Cited

U.S. PATENT DOCUMENTS 5,093,370 A * 3/1992 Kimura et al. ............... 514/643
6,368,607 B1 * 4/2002 Rerek et al. .................. 424/401

* cited by examiner

*Primary Examiner* — Gina C Yu
(74) *Attorney, Agent, or Firm* — William J. Davis; Thompson Hine LLP

(57) ABSTRACT

A concentrate including, by weight (a) 10% to 60%, preferably 25% to 35%, of a saturated fatty acid selected from stearic or palmitic acid, or mixtures thereof, in an adduct of an amidopropyldimethyl-2-hydroxyethyl ammonium halide, with substantially no free acid present, and (b) 40% to 90%, preferably 65% to 75%, of a low molecular weight alcohol or saturated fatty alcohol or alcohols, for use in personal care products, including hair care and skin care compositions.

19 Claims, No Drawings

PERSONAL CARE COMPOSITIONS

CROSS-REFERENCE TO RELATED PATENTS AND APPLICATIONS

The present application claims benefit of U.S. Provisional Application No. 60/598,211, filed Aug. 2, 2004.

This application is related to U.S. Pat. No. 6,368,607, granted to the same assignee as herein.

BACKGROUND OF THE INVENTION

1. Field of the Invention

This invention relates to personal care products, including hair and skin compositions, and more particularly, to a concentrate for use in such products, which provides advantageous performance characteristics for the user.

2. Description of the Prior Art

M. Rerek et al., in U.S. Pat. No. 6,368,607 described a product-structurant composition for personal care formulations, particularly skin care formulations, in the form of a cationic bilayer lamellar gel network, which had a strong affinity for human skin, so that the interaction between the skin and the lamellar gel provided excellent skin coverage, effective skin conditioning and long-lasting barrier enhancement.

The product-structurant composition disclosed by Rerek formed a bilayer lamellar gel network in an oil-in-water system; it included (a) a cationic swellant which was a fatty acid adduct of amidopropyldimethyl-2-hydroxyethyl ammonium halide, and (b) a gellant blend of low HLB emulsifiers having a resultant HLB of 1.5 to 4.5. Typically, the fatty acid in the adduct was stearic or palmitic acid, or mixtures thereof, and the gellant blend comprised fatty alcohols and esters and saturated fatty acids. Suitably, (a) was present in an amount of 0.5 to 5 wt. % of the composition, and (b) was the rest of the composition.

Accordingly, it is an object of this invention to provide a new and improved concentrate which is particularly suitable for use in personal care products including hair and skin care compositions.

Another object of this invention is to provide a concentrate which includes, by weight, (a) 10% to 60%, preferably 25% to 35%, of a saturated fatty acid selected from stearic or palmitic acid, or mixtures thereof, in an adduct of an amidopropyldimethyl-2-hydroxyethyl ammonium halide, with substantially no free acid present, and (b) 40% to 90%, preferably 65% to 75%, of an alcohol, preferably a saturated fatty alcohol or alcohols.

Yet another object of this invention is to provide a process for making this concentrate, particularly with substantially no free fatty acid, i.e., <1% free fatty acid, and <100 ppm, preferably <10 ppm, and most preferably <1 ppm, of residual 2-chloroethanol (ethylene chlorohydrin, ECH) reactant therein.

SUMMARY OF THE INVENTION

What is described herein is a concentrate including, by weight, (a) 10% to 60%, preferably 25% to 35%, most preferably 29-31%, of a saturated fatty acid selected from stearic or palmitic acid, or mixtures thereof, in an adduct of an amidopropyldimethyl-2-hydroxyethyl ammonium halide, with substantially no free acid present, and (b) 40% to 90%, preferably 65% to 75%, most preferably 69-71%, of an alcohol, preferably a saturated fatty alcohol or alcohols.

Preferably, (b) is cetearyl alcohol or behenyl alcohol, or mixtures thereof, most preferably a mixture of about half of cetearyl and about half of behenyl alcohol. Cetearyl alcohol itself is a mixture of cetyl and stearyl alcohols. However, low molecular weight alcohols such as propylene glycol, butylene glycol or isopropyl alcohol may be used as well.

The concentrate of the invention is made by reacting stearic or palmitic acid, or mixtures thereof, with 3-dimethylaminopropyl amine (DMAPA), at a first temperature of about 160 to 170° C., until the conversion of acid to Amide Intermediate is at least 97%, preferably 99%, which usually takes about 5-7 hours, removing excess DMAPA under vacuum to a residual level of 0.1% or less, cooling the contents to about 80 to 120° C., charging the alcohol, i.e., a low molecular weight alcohol such as propylene glycol or a saturated fatty alcohol or alcohols, and 2-chloroethanol (ethylene chlorohydrin, ECH), optionally including a stabilizer such as triisodecylphosphite, and heating the reactants to a second temperature of 145 to 155° C. for a period of time to obtain an ionic chloride level that corresponds to 2.4-2.5% in the most preferred concentrate. Thereafter residual ECH is removed under vacuum, or by sparging with dry steam, at a wall temperature of 140° C. or below.

The concentrate is obtained preferably in the form of a light yellow liquid or low melting white to cream colored solid with <1% free acid. The residual ECH level therein is <100 ppm, preferably <10 ppm, and most preferably <1 ppm.

Suitable hair and skin care products may then be formulated which include the invention concentrate, suitably in an amount of 0.1-20% by weight of concentrate in the composition, preferably 1-10%, and most preferably 2-5%.

Such hair care formulations include, but are not limited to, shampoos, conditioners, rinses, styling products, leave-in conditioners, gels, mousses, hair sprays, styling creams, non-aerosol mousses, hair dyes, relaxers, perms, and delivery systems. Such hair care formulations may also include polymers and/or surfactants, if desired.

Suitable skin care formulations include creams and lotions, moisturizing sprays, sunscreen formulas, alpha-hydroxy acid lotions, body washes, delivery systems and the like.

In general the concentrate finds advantageous application as a product structurant, an emulsion stabilizer, delivery system for active ingredients, rheology modifier, yield value booster for suspending particulates or insoluble oil droplets, to provide for consumers end benefits of conditioning for skin and hair, with antistatic properties, combability, shine, etc.

The invention will now be described in more detail with reference to the following examples.

EXAMPLE 1

Quaternization in Cetearyl Alcohol Final Concentrate in 1:1 Cetearyl/Behenyl Alcohols Part A. Preparation of Amide Intermediate (N-[3-(dimethylamino)propyl]-hexadecanamide and N-[3-(dimethylamino)propyl]-octadecanamide)

A 2-L, four-neck, round-bottom flask—equipped with a heating mantle/temperature controller, internal (batch) and external (jacket) thermocouples, mechanical stirrer, distilling adapter/Liebig condenser/receiver, vacuum take off, nitrogen inlet and sampling port—was charged with 834.5 g (3.10 mol) of triple pressed stearic acid (TPSA). A dropping funnel was installed in the sampling port; it was fitted with a stainless steel tube that extended below the surface of the liquid. The batch was heated to 75° C. to melt the TPSA, and then the stirrer was started. Air was removed from the system with three cycles of evacuation/nitrogen fill, and a nitrogen sweep of 0.05 scfh was set. The batch was heated to 150° C., and then 396.0 g (3.875 mol, 1.25 equiv) of N,N-dimethylaminopropylamine (DMAPA) was added dropwise over 2 h (ca. 4 mL/min). The batch temperature increased to 160° C., owing to the heat of reaction. The temperature was maintained at 160° C. for 1 h, then at 165° C. for 1 h, and finally 170° C. for 3 h. A sample had an acid value of 4.08 mg KOH/g (97.4% conversion). The in-process specification for % conversion was 97% min. The batch was cooled to 160° C., and a nitrogen sparge of 0.5 scfh was set. Vacuum was applied gradually until it reached 50 torr, and it was maintained for 1 h at 160° C. The vacuum was broken with nitrogen, and the batch sampled for % DMAPA by GLC; it was <0.1% by peak areas. The batch was cooled to 100° C. and flaked.

Part B. Preparation of Concentrate—Stearic Acid Quat (SAQ) (1-Propanaminium, 3-amino-N-(2-hydroxyethyl)-N,N-dimethyl-N-Cl$_{16-18}$ acyl Derivs., Chloride)

The distilling adapter/Liebig condenser/receiver in Part A was replaced with a Claisen adapter/reflux condenser. The flask was charged with 175 g (0.50 mol) of Amide Intermediate, 213 g of cetearyl alcohol, and 0.65 g of triisodecylphosphite. The batch was heated to 90° C. to melt it, air was removed from the system with three cycles of evacuation/nitrogen fill, and a nitrogen sweep of 0.05 scfh was set. The stirrer was started, and 38.2 g (0.475 mol, 0.95 equiv) of ethylene chlorohydrin (ECH) was added. The batch was heated to 150° C., and it was held there for 4 h, during which time the jacket temperature did not exceed 165° C. The batch was sampled for ionic chloride, which was 3.77%.

Part C. Removal of Ethylene Chlorohydrin (ECH)

The nitrogen sweep was set at 0.5 scfh, and the batch from Part B was cooled to 120° C. The Claisen adapter/reflux condenser was replaced with a distilling adapter/Liebig condenser/receiver. Vacuum was phased in until the system pressure was 20 torr, and the temperature was held at 120-125° C. for 4 h, during which time the jacket temperature was not allowed to exceed 135° C. The vacuum was broken with nitrogen, and 213 g of liquid behenyl alcohol was added. After mixing for 15 min, the batch was sampled for analysis. The residual ECH level was 0.55 ppm by GLC headspace analysis. The ionic chloride was 2.53%, which corresponds to 30.9% SAQ in 1:1 cetearyl/behenyl alcohol.

EXAMPLE 2

Quaternization in Behenyl Alcohol Concentrate in Behenyl Alcohol

A 175-g portion of the Amide Intermediate from Example 1, Part A was used along with 213 g of behenyl alcohol and 0.65 g of triisodecylphosphite in the same procedure as Example 1, Part B to give material with an ionic chloride of 3.80%. It was treated as in Example 1, Part C to afford a product with a residual ECH level of 'none detected' (<0.5 ppm detection limit) by GLC headspace analysis and an ionic chloride of 2.54%, which corresponds to 31.1% SAQ in behenyl alcohol.

EXAMPLE 3

Removal of ECH by Azeotropic Distillation Concentrate in Behenyl Alcohol

Part A. Preparation of Amide Intermediate

This procedure was the same as in Example 1, Part A.

Part B. Preparation of Concentrate in Behenyl Alcohol

A 353-g portion (1.00 mol) of the Amide Intermediate from Example 1, Part A was charged along with 80.5 g (1.00 mol, 1.00 equiv) of ECH, 868 g of behenyl alcohol and 0.43 g of triisodecylphosphite, and the batch was held at 140° C. for 3 h (ionic chloride, 2.26%), using the same protocol as in Example 1, Part B.

Part C. Removal of ECH by Azeotropic Distillation

A nitrogen sparge of 0.5 scfh was set, and the Claisen adapter/reflux condenser was replaced with a distilling adapter/Liebig condenser/receiver. Vacuum was phased in until the system pressure was 100 torr, and the temperature was held at 140° C. for 1 h. The vacuum was broken with nitrogen, and 130 g (10% w/w) of water was added dropwise to the batch over 1 h at 140° C., and then atmospheric pressure distillation was continued for 1 h at 150° C. Vacuum was phased in until the system pressure was 100 torr, and the temperature was held at 150° C. for 1 h. The residual ECH level was 'none detected' by GLC (ca. 50 ppm limit of detection without headspace analyzer). The ionic chloride was 2.33%, which corresponds to 28.5% SAQ in behenyl alcohol.

EXAMPLE 4

Removal of ECH by Steam Stripping Final Concentrate in 1:1 Cetearyl/behenyl Alcohols A solution of Stearic Acid Quat (SAQ) in cetearyl alcohol (ionic chloride, 3.85%) was prepared analogously to Example 1, Part B. The ECH was rereduced to 0.66 ppm by introducing 'dry' steam at the bottom of the reactor while applying 'house vacuum' (ca. 150 torr) at a batch temperature of 120° C. for 4 h. Behenyl alcohol was then added as in Example 1, Part C to give material with an ionic chloride of 2.58%, which corresponds to 31.5% SAQ in 1:1 cetearyl/behenyl alcohols.

EXAMPLE 5

Quaternization in Isopropyl Alcohol Final Concentrate in 1:1 Cetearyl/behenyl Alcohols Part A. Preparation of Amide Intermediate This procedure was the same as in Example 1, Part A.

Part B. Preparation of Concentrate in Isopropyl Alcohol (IPA)

A 2-L stainless steel autoclave was charged with 177 g (0.50 mol) of Amide Intermediate, 44.3 g (0.55 mol, 1.1 equiv) of ethylene chlorohydrin (ECH), and 410 g of IPA. The autoclave was sealed, air was removed with three cycles of pressurization/release with nitrogen, and the stirrer was started. The temperature was increased to 135° C. and held there for 6 h. The autoclave was cooled to 25° C., and the contents were discharged into a 1-L, four-neck, round-bottom flask, equipped as in Example 1, Part A. The ionic chloride was 2.47%.

Part C. Removal of Ethylene Chlorohydrin (ECH)

A nitrogen sweep of 0.5 scfh was set, and the batch from Part B was heated to 125° C. (140° C. jacket) for 3 h to remove the bulk of the IPA (>99%). The system was evacuated slowly to 20 torr and maintained at 120-125° C. (140° C. maximum jacket temperature) for 2 h. The vacuum was broken with nitrogen, and the batch was sampled for analysis. The residual ECH level was 4.8 ppm.

A 200-g portion of fresh IPA was added, and the batch was mixed for 1 h at 70-75° C. to attain a homogeneous solution of 47% SAQ in IPA.

The batch was heated to 100-125° C. (140° C. jacket temperature) for 2 h to remove 191 g of IPA (>95%). The system was evacuated slowly to 20 torr and maintained at 120-125° C. (140° C. maximum jacket temperature) for 2 h. The vacuum was broken with nitrogen, and the batch was sampled for analysis. The residual ECH level was 0.93 ppm.

Cetearyl alcohol (190 g) and behenyl alcohol (190 g) were added at 120° C., and the mixture was stirred for 1 h. The ionic chloride was 2.59%, which corresponds to 31.7% SAQ in 1:1 cetearyl/behenyl alcohol.

EXAMPLE 6

Quaternization in Isopropyl Alcohol Final Concentrate in 1:2 Cetearyl/behenyl Alcohols Part A. Preparation of Amide Intermediate This procedure was the same as in Example 1, Part A.

Part B. Preparation of Concentrate in Isopropyl Alcohol (IPA)

A 2-L stainless steel autoclave was charged with 175 g (0.50 mol) of Amide Intermediate, 38.2 g of ethylene chlorohydrin (ECH), 213 g of IPA, and 0.65 g of triisodecylphosphite. The autoclave was sealed, air was removed with three cycles of pressurization/release with nitrogen, and the stirrer was started. The temperature was increased to 150° C. and held there for 4 h. The autoclave was cooled to 25° C., and the contents were discharged into a 1-L, four-neck, round-bottom flask, equipped as in Example 1, Part A.

Part C. Removal of Ethylene Chlorohydrin (ECH)

A nitrogen sweep of 0.5 scfh was set, and the batch from Part B was heated to 110-120° C. (130° C. jacket) for 2 h to remove the bulk of the IPA (>90%). The system was evacuated slowly to 20 torr and maintained at 120-125° C. (130° C. maximum jacket temperature) for 4 h. The vacuum was broken with nitrogen, and the batch was sampled for analysis. The residual ECH level was 2.9 ppm.

A 200-g portion of fresh IPA was added, and the batch was mixed for 1 h at 70-75° C. to attain homogeneity. The batch was heated to 100-115° C. (130° C. jacket temperature) for 2 h to remove 100 g of IPA (50%). Cetearyl alcohol (141 g) and behenyl alcohol (282 g) were added. The batch was heated to 100-115° C. (130° C. jacket) for 2 h to remove 67 g of IPA. The system was evacuated slowly to 20 torr and maintained at 120-125° C. (130° C. maximum jacket temperature) for 4 h. The vacuum was broken with nitrogen, and the batch was sampled for analysis. The residual ECH level was 'none detected' (<0.5 ppm) by GLC headspace analysis. The ionic chloride was 2.44%, which corresponds to 29.8% SAQ in 1:2 cetearyl/behenyl alcohol.

EXAMPLE 7

Quaternization in Isopropyl Alcohol Final Concentrate in 2:1 Cetearyl/behenyl Alcohols Part A. Preparation of Amide Intermediate This procedure was the same as in Example 1, Part A.

Part B. Preparation of Concentrate in Isopropyl Alcohol (IPA)

A 2-L stainless steel autoclave was charged with 177 g (0.50 mol) of Amide Intermediate, 40.3 g (0.50 mol, 1.0 equiv) of ethylene chlorohydrin (ECH), 217 g of IPA, and 0.65 g of triisodecylphosphite. The autoclave was sealed, air was removed with three cycles of pressurization/release with nitrogen, and the stirrer was started. The temperature was increased to 145° C. and held there for 4 h. The autoclave was cooled to 25° C., and the contents were discharged into a 1-L, four-neck, round-bottom flask, equipped as in Example 1, Part A.

Part C. Removal of Ethylene Chlorohydrin (ECH)

A nitrogen sweep of 0.5 scfh was set, and the batch from Part B was heated to 100-125° C. (140° C. jacket) for 2 h to remove the bulk of the IPA (>95%). The system was evacuated slowly to 20 torr and maintained at 120-125° C. (140° C. maximum jacket temperature) for 4 h. The vacuum was broken with nitrogen, and the batch was sampled for analysis. The residual ECH level was 'none detected' (<0.5 ppm) by GLC headspace analysis.

A 200-g portion of fresh IPA was added, and the batch was mixed for 1 h at 70-75° C. to attain homogeneity. The batch was heated to 115-125° C. (140° C. jacket temperature) for 1 h to remove 100 g of IPA (50%). Cetearyl alcohol (283 g) and behenyl alcohol (141 g) were added. The batch was heated to 100-120° C. (140° C. jacket) for 2 h to remove 72 g of IPA. The system was evacuated slowly to 20 torr and maintained at 120-125° C. (140° C. maximum jacket temperature) for 4 h. The vacuum was broken with nitrogen, and the batch was sampled for analysis. The residual ECH level was 0.66 ppm by GLC headspace analysis. The ionic chloride was 2.46%, which corresponds to 30.1% SAQ in 2:1 cetearyl/behenyl alcohol.

EXAMPLE 8

Quaternization in Isopropyl Alcohol Final Concentrate in Behenyl Alcohol

Part A. Preparation of Amide Intermediate

This procedure was the same as in Example 1, Part A.

Part B. Preparation of Concentrate in Isopropyl Alcohol (IPA)

A 2-L stainless steel autoclave was charged with 177 g (0.50 mol) of Amide Intermediate, 44.3 g (0.55 mol, 1.1 equiv) of ethylene chlorohydrin (ECH), 221 g of IPA, and 0.65 g of triisodecylphosphite. The autoclave was sealed, air was removed with three cycles of pressurization/release with nitrogen, and the stirrer was started. The temperature was increased to 140° C. and held there for 6 h. The autoclave was cooled to 25° C., and the contents were discharged into a 1-L, four-neck, round-bottom flask, equipped as in Example 1, Part A.

Part C. Removal of Ethylene Chlorohydrin (ECH)

A nitrogen sweep of 0.5 scfh was set, and the batch from Part B was heated to 100-125° C. (140° C. jacket) for 2 h to remove the bulk of the IPA (>93%). The system was evacuated slowly to 20 torr and maintained at 120-125° C. (140° C. maximum jacket temperature) for 2 h. The vacuum was broken with nitrogen, and the batch was sampled for analysis. The residual ECH level was 2.4 ppm.

A 200-g portion of fresh IPA was added, and the batch was mixed for 1 h at 70-75° C. to attain homogeneity. The batch was heated to 90-120° C. (140° C. jacket) for 2 h to remove 100 g of IPA (50%). Behenyl alcohol (423 g) was added, and the batch was heated to 100-125° C. (140° C. jacket) for 2 h to remove 78 g of IPA. The system was evacuated slowly to 20 torr and maintained at 125-130° C. (140° C. maximum jacket temperature) for 4 h. The vacuum was broken with nitrogen, and the batch was sampled for analysis. The residual ECH level was 1.6 ppm by GLC headspace analysis. The ionic chloride was 2.55%, which corresponds to 31.2% SAQ in behenyl alcohol. After standing a room temperature for 1 week, the ECH level was 0.84 ppm.

EXAMPLE 9

Quaternization in Isopropyl Alcohol Final Concentrate in Cetearyl Alcohol

When the procedure of Example 7 was repeated with the modification that the jacket temperature during the IPA strip was 150-160° C., the final ECH level was 6.0 ppm. Cetearyl alcohol (443 g) was used instead of the mixture of cetearyl and behenyl alcohols, and the ionic chloride was 2.20%, which corresponds to 26.9% SAQ in cetearyl alcohol.

EXAMPLE 10

Removal of ECH by Azeotropic Distillation Final Concentrate in Propylene Glycol

Part A. Preparation of Amide Intermediate

This procedure was the same as in Example 1, Part A.

Part B. Preparation of Concentrate in propylene glycol

A 1-L, four-neck, round-bottom flask equipped as in Example 1, Part B was charged with 282 g (0.80 mol) of Amide Intermediate, 231 g of propylene glycol, and 0.12 g of triisodecylphosphite. The batch was heated to 90° C., air was removed from the system with three cycles of evacuation/nitrogen fill, and a nitrogen sweep of 0.05 scfh was set. The stirrer was started, and 64.4 g (0.80 mol, 1 equiv) of ECH was added. The batch was heated to 140° C., and it was held there for 3 h. The batch was sampled for ionic chloride, which was 4.71%.

Part C. Removal of Ethylene Chlorohydrin (ECH)

The 1-L, four-neck, round-bottom flask was equipped as in Example 1, Part C, and a nitrogen sparge of 0.5 scfh was set. Water (60 g, 10% w/w) was added dropwise to the batch over 1 h at 140° C., and then it was heated to 150° C. and held for 2 h. The batch was cooled to 140° C. and 120 g (20% w/w) of water was added dropwise over 1 h at 140° C. The temperature was increased to 150° C. and held for 2 h. The ECH level was 35 ppm by GLC analysis. The ionic chloride was 4.96, which corresponds to 60% SAQ in propylene glycol.

Typical hair and skin care products which include the invention concentrate are described below; however, the invention is not to be considered as limited thereto.

EXAMPLE 11

Hair Conditioner—Rinse for Normal Hair

| Ingredients | % w/w |
|---|---|
| Phase A | |
| Concentrate of Example 1 | 4.0 |
| Lanette O (Cetearyl Alcohol) | 2.0 |
| Glyceryl Stearate and PEG-100 Stearate | 1.0 |
| Phase B | |
| Water | 86.20 |
| Hydroxyethylcellulose (Natrosol HHR250 CS) | 0.5 |
| PEG 150/Stearyl Alcohol/SDMI Copolymer (Aculyn 46) | 4.0 |
| Disodium EDTA | 0.25 |
| Citric Acid | 0.05 |
| Phase C | |
| Hydrolyzed Collagen 9 Crotein C) | 1.0 |
| Amodimethicone (Si-Tec AME 656) | 0.5 |
| Propylene Glycol (and) Diazolidinyl Urea (and) Iodopropynyl Butylcarbamate (Liquid Germall Plus) | 0.5 |
| Total | 100.00% |

Procedure:
1. Heat Phase A to 65-75° C.
2. Heat Phase B also to 65° C.-75° C. with mixing until uniform.
3. Continue mixing and add Phase A to Phase B.
4. Continue mix and cool to 45° C. and add Phase C in order.
5. Continue mix until uniform and cool to room temperature.

EXAMPLE 12

Hair Conditioner—Rinse for Fine Hair

| Ingredients | % w/w |
|---|---|
| Phase A | |
| Concentrate of Example 1 | 2.3 |
| Lanette O (Cetearyl Alcohol) | 0.25 |
| Isoceteth-20 (Arlasolve 200) | 0.5 |
| Steareth-10 (Volpo S-10) | 0.5 |

-continued

| Ingredients | % w/w |
|---|---|
| Phase B | |
| Water | 85.97 |
| Hydroxyethylcellulose (Natrosol HHR 250 CS) | 0.50 |
| PEG 150/Stearyl Alcohol/SDMI Copolymer (Aculyn 46) | 8.33 |
| Disodium EDTA | 0.10 |
| Citric Acid | 0.05 |
| Phase C | |
| Amodimethicone (Si-Tec AM 656) | 0.50 |
| Wheat Amino Acid (Hydrotriticum WAA) | 0.50 |
| Liquid Germall Plus | 0.50 |
| Total | 100.00% |

Procedure:
1. Heat Phase A to 65-75° C.
2. Heat Phase B also to 65-75° C. with mixing until uniform.
3. Continue mixing and add Phase A to Phase B.
4. Continue mix and cool to 45° C. and add Phase C in order.
5. Continue mix until uniform and cool to room temperature.

EXAMPLE 13

Hair Conditioner—Rinse for Fine Hair

| Ingredients | % w/w |
|---|---|
| Phase A | |
| Concentrate of Example 1 | 2.0 |
| Lanette O (Cetearyl Alcohol) | 3.0 |
| Glyceryl Stearate and PEG-100 Stearate (Arlacel 165) | 2.0 |
| Phase B | |
| Water | 90.88 |
| Hydroxyethylcellulose (Natrosol HHR 250 CS) | 0.5 |
| Disodium EDTA (Versene NA) | 0.1 |
| Citric Acid | 0.02 |
| Phase C | |
| Cyclopentasiloxane (Si-Tec CM 040) | 0.5 |
| Wheat Amino Acid (Hydrotriticum WAA) | 0.5 |
| Liquid Germall Plus | 0.5 |
| Total | 100.00% |

Procedure:
1. Heat Phase A to 65-75° C.
2. Heat Phase B also to 65-75° C. with mixing until uniform.
3. Continue mixing and add Phase A to Phase B.
4. Continue mix and cool to 45° C. and add Phase C in order.
5. Continue mix until uniform and cool to room temperature.

EXAMPLE 14

Spray-On Detangler For Hair

| Ingredients | % w/w |
|---|---|
| Concentrate of Example 1 | 3.3 |
| Water | 94.2 |
| Amodimethicone (Si-Tec AM 656) | 1.0 |
| Wheat amino acid (Hydrotriticum WAA) | 1.0 |
| Liquid Germall Plus | 0.5 |
| Total | 100.00% |

Procedure:
1. Heat water to 45-50° C.
2. With mixing add Concentrate.
3. Continue mix and heat to 65-75° C.
4. Continue mix, cool to 45° C., and add rest of ingredients.
5. Continue mix and cool to room temperature.

EXAMPLE 15

Leave-in Conditioner for Hair

| Ingredients | % w/w |
|---|---|
| Phase A | |
| Water | 90.15 |
| PEG 150/Decyl Alcohol/SDMI Copolymer (Aculyn 46) | 3.00 |
| Disodium EDTA (Versene NA) | 0.10 |
| Hydroxyethylcellulose (Natrosol HHR 250 CS) | 0.50 |
| Phase B | |
| Concentrate of Example 1 | 4.00 |
| Glyceryl Stearate and PEG-100 Stearate (Arlacel 165) | 0.50 |
| Cetearyl Alcohol (Lanette O) | 0.25 |
| Phase C | |
| Wheat Amino Acid (Hydrotriticum WAA) | 0.50 |
| Amodimethicone (Si-Tec AM 656) | 0.50 |
| Liquid Germall Plus | 0.50 |
| Total | 100.00% |

Procedure:
1. Heat Phase A to 65-75° C.
2. Heat Phase B also to 65-75° C. with mixing until uniform.
3. Continue mixing and add Phase A to Phase B.
4. Continue mix, and cool to 45° C., and add Phase C in order.
5. Continue mix until uniform and cool to room temperature.

EXAMPLE 16

Conditioner—Styling Lotion for Hair

| Ingredients | 73A % w/w | 73B % w/w |
|---|---|---|
| Phase A | | |
| Concentrate of Example 1 | 8.0 | 8.0 |
| Ceraphyl 230 (Diisopropyl Adipate) | 10.0 | 0.0 |
| Lanette O (Cetaryl Alcohol) | 2.0 | 0.0 |
| Steareth 10 | 1.0 | 0.0 |
| Arlacel 165 (Glyceryl Stearate and PEG-100 Stearate) | 2.5 | 0.0 |

-continued

| Ingredients | 73A % w/w | 73B % w/w |
|---|---|---|
| Phase B | | |
| Water | 73.0 | 91.5 |
| Phase C | | |
| Conditioneze-7 | 3.0 | 0.0 |
| Liquid Germall Plus | 0.5 | 0.5 |
| Total | 100.0% | 100.0% |

Procedure:
1. Heat Phase A to 75° C. and heat Phase B to 75° C.
2. With agitation add Phase A to Phase B.
3. Continue mix and cool to 45° C.
4. Add Phase C ingredients.
5. Continue mix until uniform and cool to room temperature.

EXAMPLE 17

Pearlescent Conditioning Shampoo

| Ingredients | % w/w |
|---|---|
| Phase A | |
| Concentrate of Example 1 | 1.00 |
| Water | 49.80 |
| Phase B | |
| Cocoamidopropylbetaine (Miranol CB) | 10.00 |
| Polyquaternium 7 (Conditioneze) | 3.20 |
| 25% Citric Acid | 0.50 |
| Phase C | |
| Sodium Laureth 2 Sulfate (hodopex ES2) | 17.50 |
| Ammonium Lauryl Sulfate (Standapol A) | 17.50 |
| Liquid Germall Plus | 0.50 |
| Total | 100.00% |

Procedure:
1. Heat water to 45-50° C.
2. With agitation add Concentrate.
3. Continue agitation and heat to 75° C.; hold at 75° C. for 5-10 min.
4. Continue mix and cool to 45° C.
5. Continue mix and add rest of ingredients in order.
6. Continue mix until uniform and cool to RT.

EXAMPLE 18

Hair Conditioner—Rinse for Damaged Hair

| Ingredients | % w/w |
|---|---|
| Phase A | |
| Concentrate of Example 1 | 6.6 |
| Lanette O (Cetaryl Alcohol) | 4.0 |
| Glyceryl Stearate and PEG-100 Stearate | 1.0 |
| Vitamin E Acetate | 0.5 |
| Di-ethyl panthenol (di-panthenol ethyl ether) | 0.2 |

-continued

| Ingredients | % w/w |
|---|---|
| Phase B | |
| Water | 85.65 |
| Citric Acid | 0.5 |
| Phase C | |
| Hydrolyzed Collagen (Crotein C) | 1.0 |
| Amodimethicone (Si-Tec ™ AME 656) | 0.5 |
| Liquid Germall ® Plus | 0.5 |
| Total | 100.00% |

Procedure:
1. Heat Phase A (without Vitamin E Acetate and di-panthenol) to 65-75° C.
2. Add Vitamin E acetate and di-panthenol to phase A and mix thoroughly.
3. Heat Phase B to 65-75° C. with mixing until uniform.
4. Continue mixing and add Phase A to Phase B.
5. Continue mix and cool to 45° C. and add Phase C in order.
6. Continue mix until uniform and cool to room temperature.

EXAMPLE 19

Pearlized Shampoo

| Ingredients | % w/w | |
|---|---|---|
| Phase A | | |
| Concentrate of Example 1 | 2.0 | — |
| Water | QS | QS |
| Cerasynt IP | — | 0.5 |
| Phase B | | |
| Cocamidopropyl betaine (34.5%) | 10.0 | 10.0 |
| Conditioneze-7 | 3.2 | 3.2 |
| Phase C | | |
| Sodium Lauryl Ether-2 Sulfate (25.6%) | 17.5 | 17.5 |
| Ammonium Lauryl Sulfate (29.7%) | 17.5 | 17.5 |
| Liquid Germall Plus | 0.5 | 0.5 |
| Phase D | | |
| Sodium Chloride (25%) | — | 2.0 |
| Total | 100.0% | 100.0% |

Procedure:
1. Charge water to mixing vessel and heat to 75° C. with sweep-blade agitation.
2. Add either Concentrate or Cerasynt IP and mix at elevated temperature for 10-15 minutes.
3. Premix CAPB and PQ-7 in a side vessel.
4. Remove Phase A from heat; then add Phase B with continued agitation until homogeneous.
5. Add the rest of the ingredients in the order listed.

EXAMPLE 20

Suspending Shampoo

| Ingredients | % w/w |
|---|---|
| Phase A | |
| DI Water | 51.78 |
| Cocoamphodiacetate (Miranol C2M NP) | 15.00 |
| Cocamidopropyl Betaine (Mirataine CB) | 3.52 |
| Ammonium Lauryl Sulfate (Standapol A) | 6.00 |
| Sodium Lauroyl Sarcosinate (Maprosyl 30) | 12.00 |
| $C_{12-15}$ Alkyl Lactate (Ceraphyl 41) | 0.50 |
| Phase B | |
| Concentrate of Example 1 | 4.00 |
| Glycol Stearate and Stearamide AMP (Certasynt IP) | 0.25 |
| Phase C | |
| Polyquaternium-55 (Styleze W-20) | 2.50 |
| Phase D | |
| Diazolidinyl Urea and Iodopropynyl Butylcarbamate (Germall Plus) | 0.20 |
| Citric acid (25% Solution) | 2.25 |
| Sodium Chloride (25% Solution) | 2.00 |
| Total | 100.00% |

Procedure:
1. Heat water to 70° C. with moderate sweep agitation.
2. Add remaining ingredients of Phase A in the order listed, waiting for each to become uniform before adding the next and maintaining 70° C.
3. In a separate container add ingredients of Phase B and heat to 70-75° C.; mix until uniform. Add Phase B to Phase A and mix until uniform.
4. Cool batch to 35-40° C. and add Styleze W-20; mix until uniform.
5. Cool to 35° C. and add ingredients of Phase D in order listed, mixing until uniform after each addition.
6. Cool to room temperature with slow sweep mixing.

EXAMPLE 21

Silicone Oil Pearlized Shampoo

| Ingredient | % w/w |
|---|---|
| Phase A | |
| DI Water | 46.80 |
| Concentrate of Example 1 | 2.00 |
| Phase B | |
| Si-Tec DM 60,000 Dimethicone | 2.50 |
| Sodium Alkyl Ether Sulfate, 25.6% aq. soln. (Rhodapex ES-2) | 21.88 |
| Phase C | |
| Betaine, 34.53% aq. soln. (Mirataine CB) | 10.00 |
| Conditioneze-7 | 3.20 |
| Phase D | |
| Ammonium Lauryl Sulfate, 25% aq. soln. (Rhodapon L-22/HNC Kathon) | 13.12 |
| Liquid Germall Plus | 0.50 |
| Total | 100.00% |

Procedure:
1. Heat water to 75° C. with mixing. Concentrate can be added when the temperature reaches 50° C. Hold Phase A at 75° C. for 10-15 min.
2. Mix components of Phase B together and heat to 75° C. before adding to Phase A. Allow to mix for 10 min.
3. Mix components of Phase C together and heat to 75° C. before adding to Phase A/B, and mix at 75° C. for 10 min.
4. Allow formulation mixture to cool to 60-65° C. with mixing before adding Ammonium Lauryl Sulfate.
5. Cool to 45° C. with mixing before adding Liquid Germall Plus.
6. Allow formulation to cool to room temperature with mixing.

EXAMPLE 22

Firming AHA Lotion for Skin

| Ingredients | % w/w | g |
|---|---|---|
| Phase A | | |
| Water | 65.7 | 657.0 |
| EDTA | 0.1 | 1.0 |
| Glycerin | 2.0 | 20.0 |
| Guar Gum | 0.8 | 8.0 |
| Phase B | | |
| Glycolic Acid | 3.0 | 30.0 |
| NaOH (10%) | 8.5 | 85.0 |
| Phase C | | |
| Concentrate of Example 1 | 3.0 | 30.0 |
| Ceraphyl 375 | 5.0 | 50.0 |
| Ceraphyl ODS | 5.0 | 50.0 |
| Ceraphyl 230 | 3.0 | 30.0 |
| Emulsynt GDL | 3.0 | 30.0 |
| Hexylene Glycol | 0.3 | 3.0 |
| Phase D | | |
| Liquid Germall Plus | 0.6 | 6.0 |
| Total | 100.0% | 1000.0 |

Procedure:
1. Combine water and EDTA.
2. Pre-mix glycerin and gum; slowly add it to the batch with good mixing. Heat to 70-75° C.
3. Combine phase B and when phase A is uniform, slowly add phase B.
4. Combine phase C and heat to 70-75° C. Add phase C to phase A/B when its temperature is 70-75° C.
5. When batch is uniform, cool to 35° C. and add phase D.
6. Qs for water and mix to room temperature.

EXAMPLE 23

Skin Moisturizing Spray Lotion

| Ingredients | % w/w | g |
|---|---|---|
| Phase A | | |
| Water | 78.0 | 780.0 |
| EDTA | 0.1 | 1.0 |
| Glycerin | 2.0 | 20.0 |
| Phase B | | |
| Concentrate of Example 1 | 3.0 | 30.0 |
| Ceraphyl 375 | 5.0 | 50.0 |
| Ceraphyl ODS | 5.0 | 50.0 |
| Ceraphyl 230 | 3.0 | 30.0 |
| Emulsynt GDL | 3.0 | 30.0 |
| Hexylene Glycol | 0.3 | 3.0 |
| Phase C | | |
| Liquid Germall Plus | 0.6 | 6.0 |
| Total | 100.0% | 1000.0 |

Procedure:
1. Combine phase A with good mixing. Heat to 70-75° C.
2. Combine phase B and heat to 70-75° C.
3. Add phase B to phase A with mixing.
4. When batch is uniformed cool to 35° C. and add phase C.
5. Qs for water lost and mix to room temperature.

EXAMPLE 24

Moisturizing Lotion for Skin

| Ingredients | % w/w | g |
|---|---|---|
| Phase A | | |
| Water | 79.1 | 791.0 |
| EDTA | 0.1 | 1.0 |
| Glycerin | 2.0 | 20.0 |
| Phase B | | |
| Concentrate of Example 1 | 3.0 | 30.0 |
| Ceraphyl 424 | 2.0 | 20.0 |
| Ceraphyl 140 | 2.00 | 20.0 |
| Ceraphyl 368 | 3.0 | 30.0 |
| Ceraphyl 230 | 3.0 | 30.0 |
| Emulsynt GDL | 3.0 | 30.0 |
| Hexylene Glycol | 0.3 | 3.0 |
| Phase C | | |
| Orchid Complex OS | 1.5 | 15.0 |
| Liquid Germall Plus | 0.6 | 6.0 |
| Fragrance | 0.4 | 4.0 |
| Total | 100.0% | 1000.0 |

Procedure:
1. Combine phase A in beaker with good mixing. Heat to 70-75° C.
2. Combine phase B and heat to 70-75° C.
3. Add phase B to phase A with mixing.
4. When batch is uniformed cool to 35° C. and add phase C.
5. Qs for water lost and mix to room temperature.

EXAMPLE 25

Moisturizing Spray Lotion

| Ingredients | % w/w |
|---|---|
| Phase A | |
| DI Water | 74.30 |
| Versene NA | 0.10 |
| Glycerin | 1.00 |
| Phase B | |
| Concentrate of Example 1 | 3.00 |
| Ceraphyl 230 | 4.00 |
| Ceraphyl 368 | 10.00 |
| Hexylene Glycol | 1.00 |
| Phase C | |
| Liquid Germall Plus | 0.60 |
| Total | 100.00% |

Procedure:
1. Add Versene and glycerin to water. Heat phase A to 70-75° C. with stirring.
2. Combine phase B; heat to 75-80° C. until uniform.
3. When phase A is stirring at 70-75° C., add phase B to phase A with propellor. When batch appears uniform, turn off heat.
4. Continue stirring throughout cool-down. Add phase C at 35-40° C.
5. Make up for water loss and sweep to RT.

EXAMPLE 26

Medium SPF Sunscreen

| Ingredients | % w/w | g |
|---|---|---|
| Phase A | | |
| Water | 60.65 | 606.50 |
| Butylene Glycol | 2.00 | 20.00 |
| EDTA | 0.10 | 1.00 |
| Guar Gum | 0.50 | 5.00 |
| Phase B | | |
| Concentrate of Example 1 | 4.00 | 40.00 |
| Escalol 557 | 6.00 | 60.00 |
| Escalol 567 | 7.50 | 75.00 |
| Ceraphyl 41 | 5.00 | 50.00 |
| Ceraphyl 140 | 2.00 | 20.00 |
| Ceraphyl 368 | 3.00 | 30.00 |
| Phase C | | |
| Poviderm SK-3 | 1.50 | 15.00 |
| Water | 5.00 | 50.00 |
| Phase D | | |
| Si-Tec CM 040 | 2.00 | 20.00 |
| Phase E | | |
| Liquid Germall Plus | 0.75 | 7.50 |
| Total | 100.0% | 1000.0 |

Procedure:
1. Combine water and EDTA. Pre-mix glycol with gum and add it with stirring. Heat to 70-75° C.
2. Combine phase B and heat to 75-80° C.
3. Combine phase C with stirring until completely uniform.
4. Add phase B to phase A when both phases are uniformed.
5. When phase A/B is uniform add phase C.
6. Cool batch to 40° C. and add phase D with mixing.
7. Cool to 35° C. and add phase E to the batch with mixing.
8. Qs for water lost and continue to stir to RT.

EXAMPLE 27

Medium SPF Spray

| Ingredients | % w/w |
| --- | --- |
| Phase A | |
| DI Water | 75.50 |
| Versene NA | 0.10 |
| Glycerin | 1.00 |
| Phase B | |
| Concentrate of Example 1 | 3.00 |
| Ceraphyl 557 | 7.50 |
| Ceraphyl 567 | 3.00 |
| Ceraphyl 587 | 3.00 |
| Ceraphyl 368 | 6.00 |
| Hexylene Glycol | 0.30 |
| Phase C | |
| Liquid Germall Plus | 0.60 |
| Total | 100.00% |

Procedure:
1. Add Versene and glycerin to water. Begin heating phase A to 70-75° C. with stirring.
2. Combine phase B, heat to 75-80° C.
3. When phase A is stirring at 70-75° C. and phase B is uniform at 75-80° C., add phase B to phase A with propellor. When batch appears uniform, turn off heat. Continue stirring throughout cool-down.
4. Add phase C at 35-40° C.
5. Make up for water loss and sweep to RT.

EXAMPLE 28

High SPF Spray

| Ingredients | % w/w |
| --- | --- |
| Phase A | |
| DI Water | 65.80 |
| Versene NA | 0.10 |
| Glycerin | 1.00 |
| Phase B | |
| Concentrate of Example 1 | 3.00 |
| Ceraphyl 557 | 7.50 |
| Ceraphyl 567 | 6.00 |
| Ceraphyl 587 | 5.00 |
| Ceraphyl 597 | 10.00 |
| Hexylene Glycol | 1.00 |
| Phase C | |
| Liquid Germall Plus | 0.60 |
| Total | 100.00% |

Procedure:
1. Add Versene and glycerin to water. Heat phase A to 70-75° C. with stirring.
2. Combine phase B, heat to 75-80° C.
3. When phase A is stirring at 70-75° C. and phase B is uniform at 75-80° C., add phase B to phase A with propellor. When batch appears uniform, turn off heat. Continue stirring throughout cool-down.
4. Add phase C at 35-40° C.
5. Make up for water loss and sweep to RT.

KEY BENEFITS OF INVENTION

Monoalkyl quat which performs like a dialkyl quat
Vegetable-derived from triple pressed stearic acid (ca. 45:55 stearic/palmitic)
Forms stable emulsions
Self-emulsifying
Forms lamellar gel structure
Ease of rinsing with soft feel
Anti-static properties
Ease of wet and dry combing
Superior hair and skin conditioning and moisturizing
Compatible with other cationic ingredients

SUMMARY OF APPLICATIONS OF INVENTION

Leave-On Conditioners
Conditioners
Gels
Shampoo
Mouse
Hair Spray
Styling Creams
Non-Aerosol Mousse
Hair Dyes
Relaxers
Perms
Delivery System
Skin Conditioning Cremes and Lotions
Skin Moisturizing Cremes and Lotions While the invention has been described with particular reference to certain embodiments thereof, it will be understood that changes and modifications may be made which are within the skill of the art. Accordingly, it is intended to be bound only by the following claims, in which:

What is claimed is:
1. A concentrate comprising, by weight, (a) 25% to 35% of a saturated fatty acid selected from stearic or palmitic acid, or mixtures thereof, in an adduct of an amidopropyldimethyl-2-hydroxyethyl ammonium halide, with substantially no free acid present, and (b) 65% to 75% of an alcohol, selected from a low molecular weight alcohol or a saturated fatty alcohol or alcohols, or mixtures thereof wherein the concentrate has a residual ethylene chlorohydrin level of <100 ppm.

2. A concentrate according to claim 1 wherein (b) is cetearyl or behenyl alcohol, or a mixture thereof, or propylene glycol, butylene glycol or isopropyl alcohol.

3. A concentrate according to claim 1 wherein (a) is about 30% and (b) is about 70%.

4. A concentrate according to claim 2 wherein (b) is a mixture of about half of cetearyl and half of behenyl alcohols.

5. A concentrate according to claim 1 which is made by reacting stearic or palmitic acid, or mixtures thereof, with 3-dimethylaminopropyl amine (DMAPA), at a first temperature of 160° to 170° C., until the conversion of acid to adduct is 97-99%, removing excess DMAPA under vacuum, cooling the contents, charging the low molecular weight alcohol or saturated fatty alcohol or alcohols and 2-chloroethanol (ethylene chlorohydrin, ECH), and heating to a second temperature of 145 to 155° C., and removing ECH under vacuum at a wall temperature of 140° C. or below.

6. A concentrate according to claim 5 wherein the free fatty acid is <1%.

7. A concentrate according to claim 5 wherein the residual ethylene chlorohydrin level is <10 ppm.

8. A concentrate according to claim 5 wherein the residual ethylene chlorohydrin level is <1 ppm.

9. A formulation including the concentrate of claim 1 which is a hair or skin care formulation.

10. A formulation according to claim 9 including 0.1-20% by weight of said concentrate.

11. A formulation according to claim 10 including 1-10% of said concentrate.

12. A formulation according to claim 11 including 2-5% of said concentrate.

13. A hair care formulation according to claim 9 which is a shampoo, conditioner, rinse, styling lotion, leave-in conditioner, gel, mousse, hair spray, styling cream, non-aerosol mousse, hair dye, relaxer, detangler or perm.

14. A hair care formulation according to claim 13 which includes a polymer and/or a surfactant.

15. A skin care formulation according to claim 9 which is a cream, lotion, moisturizing spray, sunscreen formula, alpha-hydroxy acid lotion, or body wash.

16. A skin care formulation according to claim 15 which includes a polymer and/or a surfactant.

17. A formulation according to claim 9 which provides structurant properties therein.

18. A formulation according to claim 9 which provides a delivery system for actives.

19. A concentrate according to claim 1 wherein the concentrate has a residual level of DMAPA of 0.1% or less.

* * * * *